(12) United States Patent
Caputo

(10) Patent No.: US 10,266,870 B2
(45) Date of Patent: Apr. 23, 2019

(54) PROCESS AND SYSTEM FOR FLOW CYTOMETRY FLUORESCENT DETECTION OF REACTIVE MATERIALS IN VISCOUS NON-FILTERABLE MATERIALS

(71) Applicant: Professional Compounding Centers of America, Inc., Houston, TX (US)

(72) Inventor: Ross A. Caputo, Spring, TX (US)

(73) Assignee: Eagle Analytical Services, Inc., Houston, TX (US)

( * ) Notice: Subject to any disclaimer, the term of this patent is extended or adjusted under 35 U.S.C. 154(b) by 0 days.

(21) Appl. No.: 16/125,149

(22) Filed: Sep. 7, 2018

(65) Prior Publication Data

US 2019/0071709 A1 Mar. 7, 2019

Related U.S. Application Data

(60) Provisional application No. 62/555,505, filed on Sep. 7, 2017.

(51) Int. Cl.
| | | |
|---|---|---|
| *C12Q 1/22* | (2006.01) | |
| *C12Q 1/04* | (2006.01) | |
| *G01N 33/15* | (2006.01) | |
| *G01N 21/64* | (2006.01) | |
| *G01N 1/40* | (2006.01) | |

(52) U.S. Cl.
CPC ............... *C12Q 1/22* (2013.01); *C12Q 1/04* (2013.01); *G01N 33/15* (2013.01); *G01N 1/4005* (2013.01); *G01N 21/6428* (2013.01); *G01N 21/6486* (2013.01); *Y10T 436/255* (2015.01)

(58) Field of Classification Search
CPC ... C12Q 1/22; C12Q 1/24; C12Q 1/04; G01N 33/15; G01N 1/40; G01N 1/4005; G01N 21/64; G01N 21/6428; G01N 21/6486; Y10T 436/25; Y10T 436/25375; Y10T 436/255

USPC ......... 436/63, 164, 165, 172, 174, 177, 178; 422/82.08, 527, 534, 535; 435/4, 5, 29, 435/30, 31, 34, 287.1, 287.4, 288.7

See application file for complete search history.

(56) References Cited

U.S. PATENT DOCUMENTS

| | | | | |
|---|---|---|---|---|
| 4,477,460 | A | * | 10/1984 | Waterbury ........... A61K 31/425 514/369 |
| 5,663,057 | A | * | 9/1997 | Drocourt ............ G01N 15/1468 435/174 |
| 9,709,500 | B2 | * | 7/2017 | Wainwright ....... G01N 21/6486 |
| 2006/0134729 | A1 | | 6/2006 | Besson-Faure et al. |
| 2008/0038738 | A1 | | 2/2008 | Weigum et al. |
| 2008/0305514 | A1 | * | 12/2008 | Alford ..................... C12Q 1/04 435/34 |

(Continued)

OTHER PUBLICATIONS

Smith et al. PDA Journal of Pharmaceutical Science and Atechnology, vol. 64, 2010, pp. 356-363.*

(Continued)

*Primary Examiner* — Maureen Wallenhorst
(74) *Attorney, Agent, or Firm* — David G. Woodral; GableGotwals

(57) ABSTRACT

A method of preparing a sample for cytometry detection of viable biological contaminants includes obtaining a non-aqueous sample, obtaining a suitable solvent, and filtering the suitable solvent creating a filtered solvent. The non-aqueous sample is combined with the filtered solvent creating a mixture for cytometry testing.

17 Claims, 2 Drawing Sheets

(56) References Cited

U.S. PATENT DOCUMENTS

2013/0095521 A1* 4/2013 de Rigo .................. C12Q 1/22
                                                    435/36
2017/0044588 A1* 2/2017 Felden ............... G06K 9/00134

OTHER PUBLICATIONS

Vanhee et al. Journal of Applied Microbiology, vol. 109, 2010, pp. 1745-1752.*

De Prijck et al. Letters in Applied Microbiology, vol. 47, 2008, pp. 571-573.*

De Prijck, et al., "Comparison of Solid-Phase Cytometry and the Plate Count Method for the Evalulation of the Survival of Bacteria in Pharmaceutical Oils", "Letters in Applied Microbiology ISSN 0266-8254", 2008, pp. 571-573, vol. 47 (2008), Publisher: Journal compilation; The Society for Applied Microbiology.

Vanhee, et al., "Detection and Quantification of Bacteria and Fungi Using Solid-Phase Cytometry", "Springer Science+Business Media B.V. 2010", 2010, pp. 25-41, Publisher: Detection of Bacteria, Viruses, Parasites and Fungi: NATO Science for Peace and Security Series A: Chemistry and Biology.

International Search Report and Written Opinion Prepared by the ISA/US for PCT/US2018/050021, dated Nov. 29, 2018.

Ron Smith, et al., "Evaluation of the Scan RDI as a Rapid Alternative to the Pharmacopoeial Sterility Test Method: Comparison of the Limits of Detection", "PDA Journal of Pharmaceutical Science and Technology", Jul. 14, 2009, pp. 356-363, vol. 64.

Jones, D.L., et al., "Solid-Phase, Laser Scanning Cytometry: A New Two-Hour Method for the Enumeration of Microorganisms in Pharmaceutical Water", "Pharmacopeial Forum", 01/00/1999, pp. 7626-7645, vol. 25, No. 1, Publisher: The United States Pharmacopeial Convention, Inc.

* cited by examiner

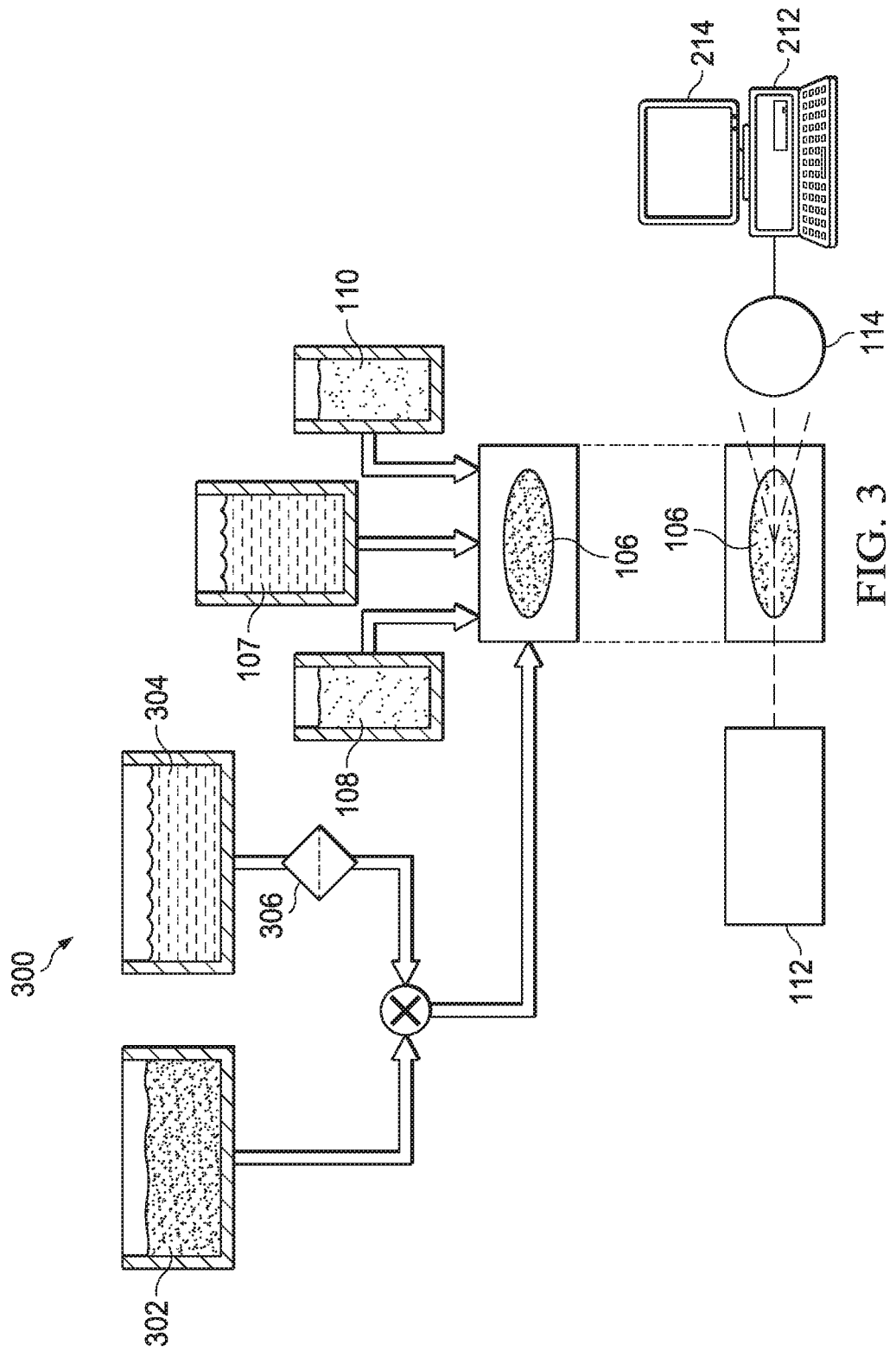

PROCESS AND SYSTEM FOR FLOW CYTOMETRY FLUORESCENT DETECTION OF REACTIVE MATERIALS IN VISCOUS NON-FILTERABLE MATERIALS

CROSS-REFERENCE TO RELATED CASES

This application claims the benefit of U.S. provisional patent application Ser. No. 62/555,505, filed on Sep. 7, 2017, and incorporates such provisional application by reference into this disclosure as if fully set out at this point.

FIELD OF THE INVENTION

The present invention relates to systems and methods for sterility testing of pharmaceutical preparations, and more particularly compounded pharmaceutical preparations.

BACKGROUND OF THE INVENTION

Finished pharmaceutical product testing required to assign the maximum allowable beyond use dates (BUD) requires a final preparation sterility test to be performed. The shelf-life of compounded pharmaceutical preparations is typically 30-60 days but is commonly less. Without an adequate sterility test (e.g., per USP <797>), room temperature stored sterile compounded drug preparations would have a labeled BUD of 4 to 6 days.

Cytometry systems may be used to detect very small quantities of contaminant such as bacterium, mold, fungi, etc. A cytometry system may be capable of detecting contamination as small as a single living cell, and the ability of the cell to multiply is not required for testing (as would be for a culture-based test). However, current cytometry systems require that the tested composition be in an aqueous preparation. Therefore oil-based preparations cannot be tested.

What is needed is a system and method for addressing the above, and related, problems.

SUMMARY OF THE INVENTION

The invention of the present disclosure, in one aspect thereof comprises a method for the detection of materials reactive to cytometry fluorescent detection in a sample. The method includes obtaining the sample, obtaining at least one suitable solvent, mixing the sample and the solvent to obtain a mixture, filtering the mixture through a membrane, preparing the membrane for presentation to a flow cytometry fluorescent detection system, and presenting the membrane to the flow cytometry fluorescent detection system for analysis to obtain results. In some methods, the materials reactive to flow cytometry fluorescent detection are viable microorganisms in a pharmaceutical preparation.

In some embodiments, the viscous non-filterable sample is an oil based pharmaceutical formulation. The solvent may be isopropyl myristate (IPM). The IPM may be filtered before mixing with the sample. The ratio of IPM to the viscous non-filterable sample in the mixture may be at least 1:1. The IPM and the viscous non-filterable sample may be mixed in a closed system, or may be mixed adjacent to the filter membrane. The IPM and the viscous non-filterable sample may be heated and stirred while mixing.

The invention of the present embodiment, in another aspect thereof, comprises a method of preparing a sample for cytometry detection of viable biological contaminants that includes obtaining a non-aqueous sample, obtaining a suitable solvent, and filtering the suitable solvent creating a filtered solvent. The method also includes combining the non-aqueous sample with the filtered solvent creating a mixture and filtering the mixture through a cytometry test membrane to isolate contaminant cells onto a test membrane.

In some embodiments, the method includes providing a viability marker to the contaminant cells on the test membrane. The viability marker may be integrated with the test membrane.

The method may include filtering the solvent through a 0.45-micron filter and/or warming the filtered solvent. The suitable solvent comprises isopropyl myristate, and the method may include diluting the sample with a suitable oil.

The step of combining the non-aqueous sample with the filtered solvent creating a mixture may be performed prior to placing the mixture onto the test membrane. In other embodiments, the step of combining the non-aqueous sample with the filtered solvent creating a mixture is performed in contact with the test membrane.

The step of filtering the mixture through a cytometry test membrane to isolate contaminant cells onto a test membrane may further comprise utilizing vacuum to filter the mixture through the cytometry test membrane. In some embodiments, the cytometry test membrane is counterstained. Cytometry testing by laser interrogation of the test membrane may be performed to determine the presence of viable biological contaminants.

BRIEF DESCRIPTION OF THE DRAWINGS

FIG. 3 is a schematic diagram of a cytometry preparation method for oil-based samples according to aspects of the present disclosure.

DETAILED DESCRIPTION OF THE PREFERRED EMBODIMENTS

Figure 1:
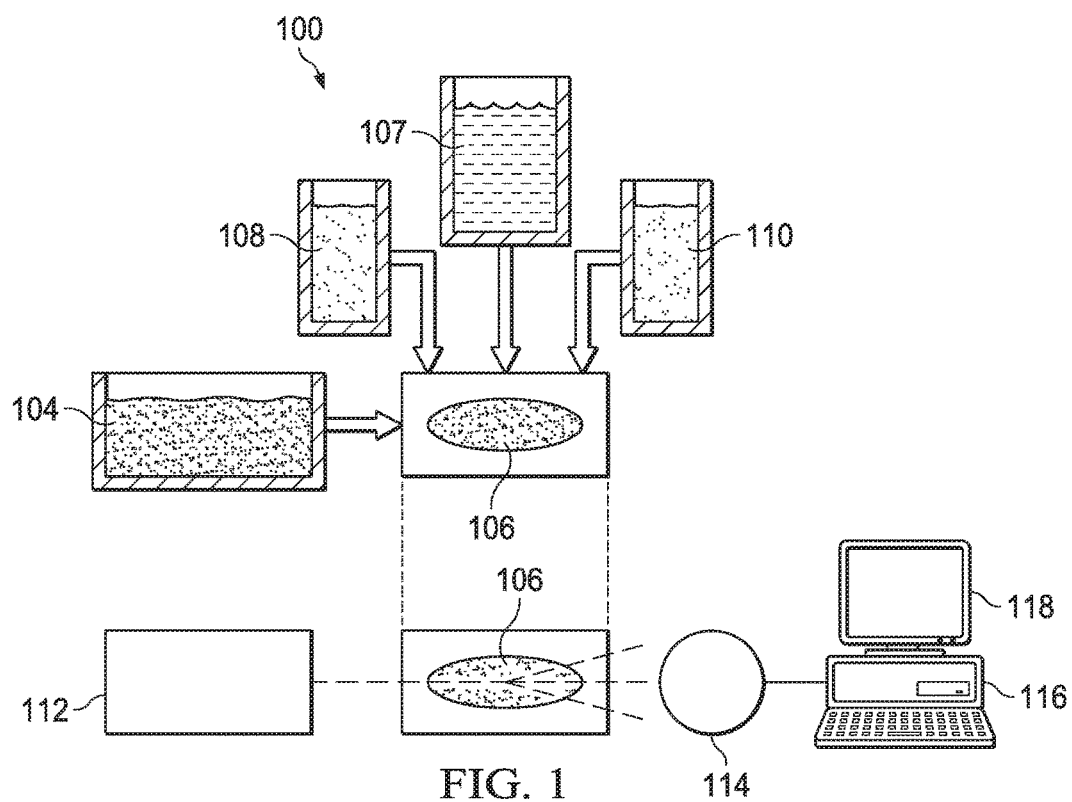
FIG. 1 is a simplified schematic diagram of a solid phase cytometry system according to aspects of the present disclosure.

The embodiments herein and the various features and advantageous details thereof are explained more fully with reference to the non-limiting embodiments that are illustrated in the accompanying drawings and detailed in the following description. Descriptions of well-known components and processes and manufacturing techniques are omitted so as to not unnecessarily obscure the embodiments herein. The examples used herein are intended merely to facilitate an understanding of ways in which the invention herein may be practiced and to further enable those of skill in the art to practice the embodiments herein. Accordingly, the examples should not be construed as limiting the scope of the claimed invention.

The United States Pharmacopeia (USP) test protocols for sterility testing is contained in USP <71>. Currently employed USP <71> sterility test procedure requires a minimum of 14 and up to 18 days for test completion. This is because a suitable requisite incubation/growth period for biological material which may have contaminated the pharmaceutical preparation. As a result, it is common that, as a result of testing, the shelf-life of the pharmaceutical preparation is reduced to 42 days, or less. It is known in the art for a drug to exceed its BUD before the currently known USP <71> test is completed. It is conceivable that, in light of this fact, drugs are used without testing. In the context of patient specific or custom compounded unique drug mixtures, expiratory dating is a problem in the industry.

Notwithstanding this fact, due to the time required to complete current protocols, lengthy inventory hold times are common in the pharmaceutical industry and particularly the compounding pharmaceutical industry. Shelf-life reductions due to inventory hold times not only translate into financial loss due to destruction of inventory from exceeding BUD parameters, but the useful life of compounded pharmaceuticals by the patient is, likewise, significantly diminished.

Proposed revisions to USP <797> will reduce current BUD for sterile compounded pharmaceutical preparations. This further BUD reduction is expected to increase the problem.

A need, therefore, exists for an alternative method for sterility testing of drugs purported to be sterile. This need extends, particularly, to custom and unique pharmaceutical compounds. In addition, a need exists for such an alternative method which comports with USP <71> or is validated pursuant to USP <1223> and/or USP <1225> to provide advantages in terms of accuracy, sensitivity, precision, selectivity, or adaptability to automation or computerized data reduction.

Flow cytometry fluorescent detection systems use a combination of fluorescent labeling and solid phase laser cytometry to identify viable microorganisms from filterable pharmaceutical samples. The sensitivity of such systems is such that they may be capable of detecting a single cell within 3 hours. Commercially available proprietary stains which consist of non-fluorescent membrane permeant substrates are used which are cleaved by non-specific esterases and retained in viable cells. This accumulated measurable chromophore is then detected during a laser scanning step by an analyzer. Within a short time, as short as 3 minutes, results are displayed without operator interpretation.

Non-aqueous preparations or samples have not been compatible with solid phase cytometry systems to date. This is due to several possible reasons. One reason is that non-aqueous samples cannot be passed through the filtering processes required for sample preparation within an acceptable period of time, or without damage to testing equipment. Some products and preparations are incompatible with this cytometry owing to the fact that they auto-fluoresce.

The present disclosure describes various embodiments of an effective and reliable test system and methodology for the detection of microorganisms in sterile compounded preparations, and particularly non-soluble sterile preparations which cannot be filtered for presentation to a flow cytometry fluorescent detection analyzer. More specifically, the present disclosure describes such a tests and methods using cytometry fluorescent detection systems for the detection of microorganisms in non-aqueous and/or non-soluble, unfilterable, sterile compounded preparations such as oil(s), creams, ointments, pastes, and the like and which may include additional oil(s). In addition, the process of the present disclosure may be used for the detection of microorganisms in non-aqueous and/or non-soluble, unfilterable material such as oils, or materials containing oils.

The methods of the present disclosure, in various embodiments, include the use of flow cytometry fluorescent detection with front end sample preparation. Using methods of the present disclosure, samples previously believed/considered unsuitable due to their inability to be filtered through a filter ranging between 0.2 μm-0.5 μm filter, (such as oil(s), creams, ointments and pastes), are treated with a solvent, (most preferably one approved for use by USP <71>), filtered, labeled and scanned using a flow cytometry fluorescent detection analyzer for the presence of microorganisms.

Unfilterable materials on a cytometry test membrane may autofluoresce thereby rendering the analysis unusable as autofluorescence causes visible "noise" such that the cytometry detector may be unable to discriminate the actual biological contaminants. As a result, the sample material must be rendered filterable without affecting the viability of any microorganisms which may be present. One object of the process of the present disclosure is the transfer of naked microorganisms, which may be present in a sample, onto cytometry filter membrane for presentation to a flow cytometry fluorescent detection system for sterility analysis.

As used herein, the terms flow cytometry, solid phase cytometry, flow cytometry fluorescent detection, FCFD, and/or pulse cytophotometry, shall mean a laser or impedance based biophysical technology employed in cell counting, cell sorting, biomarker detection and protein engineering, by suspending cells in a fluid and passing them by an electronic detection apparatus. Viable cells are labeled and labeled cells produce fluorescence. Fluorescence is detected by the analyzer. Such an analyzer includes impedance or conductivity measurement system(s), optical system(s) and detector system(s). The detector measures forward-scattered light (FSC), side-scattered light (SSC), as well as dye-specific fluorescence signals. An Analog-to-Digital Converter (ADC) converts analog measurements from the detector into digital signals that can be processed (including linear or logarithmic amplification) by a computer. One such particularly suitable cytometry fluorescence detection system is the Chemunex™ ScanRDI® analyzer available from bioMerieux, Inc., 595 Anglum Road, Hazelwood, Mo. 63042 USA, www.biomerieux-usa.com. It should be understood that, when used herein, ScanRDI® and/or ScanRDI® analyzer are included within the definition of flow cytometry fluorescent detection set forth herein.

The ScanRDI® analyzer is the subject of an FDA Type V Drug Master file (DMF 14621, incorporated herein by reference) which contains data to support the technology for the detection of bacteria, spores, yeast and molds. This master file also contains the validation data for process water microbial analysis. This system is Title 21 C.F.R. § 11 compliant. Using this process, a sterility test can be performed in one day. ScanRDI® analyzer performance supports the utilization of this method for the sterility testing of compounded pharmaceutical preparations.

The ScanRDI® system employs a combination of direct fluorescent labeling and solid phase laser scanning cytometry to rapidly enumerate viable microorganisms from a test sample. ScanRDI® may be used for sterility testing compounded sterile preparations. The ScanRDI® analyzer is an instrument capable of detecting fluorescent signals on the surface of a solid support substrate/membrane. For pharmaceutical and/or microbiological applications, the fluorescent signals reveal/indicate viable microorganisms. These viable microorganisms are previously labeled with a non-fluorescent stain (Fluorescein) which is retained in viable cells. Samples are filtered using a disposable Fluorassure Integral Filtration Unit (FIFU) device, or a CB04 filter (system), both well-known to those of skill in the art and available commercially, to trap microorganisms on a membrane which are then treated with reagents to determine their viability. Only viable organisms are capable of enzymatically cleaving the non-fluorescent stain and retaining the fluorescent end-products. A substrate component of the labeling solution enters the microorganism through the cell membrane. Living cells cleave the non-fluorescent viability substrate by an enzymatic reaction, releasing fluorescent particles (free fluorochrome) within the cell. The cell's membrane holds the light-emitting fluorochrome within the cell and allows it to fluoresce (providing a fluorescent signal) which is detected by the ScanRDI's laser. Nonliving cells are not metabolically active and not labeled. The detection of the fluorescent signal requires that: a) the instrument source of illumination (laser) is of sufficient power and is accurately focused at the surface of the membrane, and; b) the PhotoMultiplier Tube (PMT) voltages are correctly set for adequate sensitivity. This procedure allows for the detection of mesophilic bacteria, yeast, and molds including spores.

ScanRDI® is a non-growth-based technology which is sensitive enough to detect a single bacterial, yeast or mold contaminant in only three (3) hours. This analyzer provides a linear response from 1 to $10^4$ microbial cells. This flow cytometry fluorescent detection system, therefore, provides a rapid alternative to traditional 14-day sterility testing. As a result, the significant problems associated with shelf life of a compounded pharmaceutical preparation, discussed above, are avoided.

Referring now to FIG. 1, an exemplary cytometry system 100 is shown in simplified schematic. In various embodiments, cytometry systems rely on the fact that living cells will uptake and/or process specific chemicals or compositions. Some of these chemicals or compositions can then be tested for in a sample by various mechanisms. Such chemicals or compositions that can be used to test for living cellular activity are known as viability markers. Some viability markers will, for example, cause a living cell to fluoresce when exposed to specific forms of electromagnetic radiation. This may be referred to as interrogation. In some embodiments, the interrogation source is a laser. The fluorescence of the interrogated sample may be detected and analyzed by known methods to determine the presence of the target contaminant (e.g., bacterium, mold, yeast, spores, etc.).

The system of FIG. 1 may be referred to as a solid phase cytometry system. The system as shown in FIG. 1 may integrate all of part of the ScanRDI® system discussed above. Here, a sample 102 (an aqueous sample) may be passed through a test membrane 104. The test membrane 104 may act as a cell strainer to trap target contaminants for testing. Only viable contaminants are of concern with respect to sterility testing so a solution containing a viability marker 108 may also be added to or passed through the test membrane 106. In some embodiments, the viability marker 108 may be Fluorassure® available from Chemunex. In other embodiments, the viability marker 108 may be integrated with the test membrane 106 such as the FIFU (Fluorassure integrated filtration unit) product from Chemunex.

The step of preparing the membrane 106 for presentation to a flow cytometry fluorescent detection system may include rinsing the filter membrane 106 with at least one rinsing fluid 107. In one preferred embodiment, specified in USP <71>. For example, and without limitation, as is specified in USP <71>, the rinsing fluid may be one or more of Fluid A, Fluid B, Fluid D, and Fluid K or a combination thereof. Fluid A, Fluid B, Fluid D, and Fluid K are each well-known to those of skill in the art and are each available commercially from sources such as, for example MilliporeSigma Corporation. The life science business of Merck KGaA, Darmstadt, Germany operates as MilliporeSigma in the US and Canada. In one embodiment of the process of the present disclosure, the rinsing fluid is Fluid D. In another embodiment of the process of the present disclosure, the rinsing fluid is Tween 80, also available commercially from sources such as MilliporeSigma Corporation.

Prior to interrogation, the test membrane 106 may be treated with a counterstain 110 to enhance readability/detectability and contrast. The counterstain 110 may be a CSE/SCM counterstain (from CHEMUNEX) according to various embodiments.

The contaminants trapped on the test membrane 104 may be exposed to laser interrogation with laser 112. In some embodiments, the laser 112 is an argon neon laser as is known it the art for sample interrogation. A detecting apparatus 114 may detect fluorescence from living cells on the test membrane 106. The detecting apparatus 114 may rely on various photomultipliers, filters, amplifiers and other devices as are known in the art for detecting sample cell fluorescence and may be part of a ScanRDI® unit. A computer 116 may receive the data from the detecting apparatus 114 for display on a monitor 118 for review and analysis by a technician to determine levels of contamination or sterility. The number of fluorescing cells on the membrane 114 corresponds to the amount of contamination or cleanliness (sterility) of the tested sample.

Figure 2:
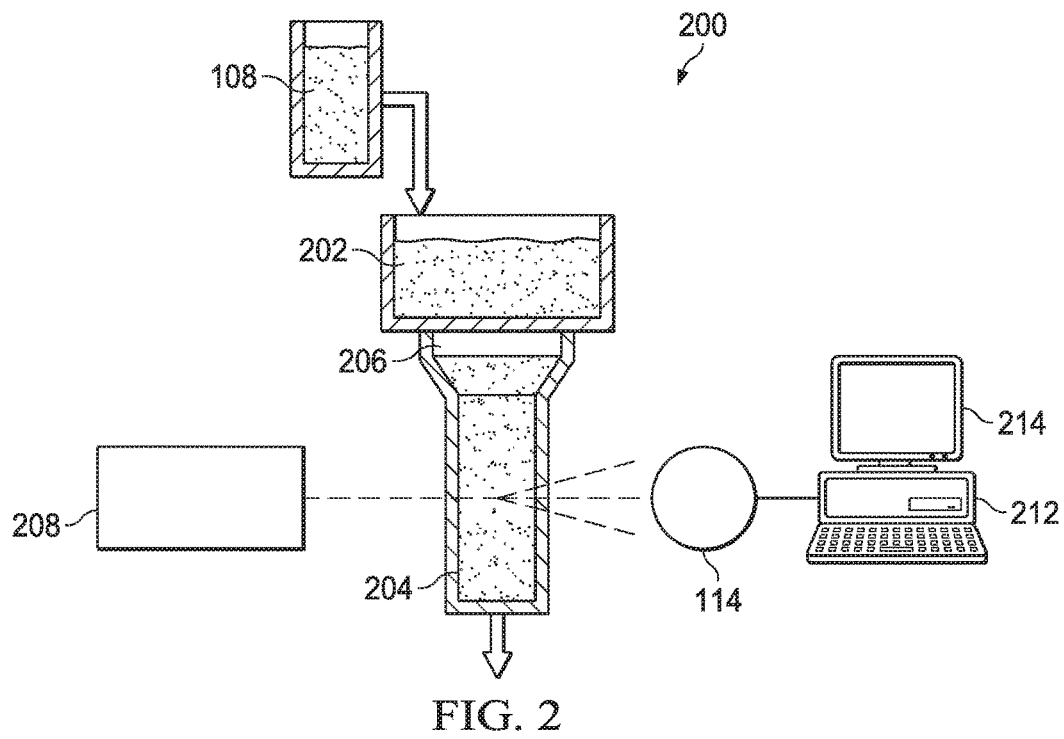
FIG. 2 is a simplified schematic diagram of a flow cytometry system according to aspect of the present disclosure.

In addition to so-called solid phase cytometry, flow cytometry provides a mechanism by which samples are tested as they flow through a tube or other test area. FIG. 2 provides a simplified schematic corresponding to such a system 200. Here a sample 202 is made to flow through very thin tube 204 that forces any contaminants to "line up" as they flow through. The sample 202 may be filtered before or as it passes into the tube 204 by a filter 206. As before a viability marker 108 may be provided into the test sample 202 to ensure fluorescence of living or viable cells and contaminants.

An interrogation laser 208 illuminates the tube 204 and fluorescence is detected by detector 210 for processing by computer 212 and/or display on monitor 214 as is known in the art. As is also known in the art, data from the computer 212 may be used to perform physical cell separation downstream of the test, or for other operations.

A known problem relating to the use of cytometry fluorescent detection systems is the inability to process liquids that are not aqueous preparations due to the fact that the detection procedure requires filtration of the product through a 0.45-micron filter (i.e., the test membrane 106). This is particularly true with respect to solid phase systems (e.g., 100, FIG. 1) but may also be a problem faced by flow cytometry methods where the sample is required to be finely filtered for any reason prior to the test protocol. As a result, previous cytometry fluorescent detection systems were unusable for sterility testing of drug compounds which are not aqueous or non-soluble preparations and, therefore, not filterable. These may include as ointments, creams, pastes and the like. The same problem arises for cytometry testing of pharmaceutical compositions/drug compounds which contain oil(s).

The present disclosure includes, various embodiments, a process for sterility testing of a non-aqueous sample. In some embodiments, the process is based on incorporation of a ScanRDI® machine. The process may include: 1) obtaining a sample for sterility testing or to be tested for the presence of viable microorganisms; 2) obtaining a suitable solvent; 3) mixing the sample and the solvent to obtain a mixture; 4) filtering the mixture through a membrane; 5) rinsing the membrane with a rinsing fluid; 6) preparing the membrane for presentation to a flow cytometry fluorescent detection system (e.g., ScanRDI®, 7) presenting the membrane to the flow cytometry fluorescent detection system for flow cytometry fluorescent detection analysis to obtain results, and; 8) determining whether the sample passes or fails the sterility test based on the results.

For the purpose of the present disclosure, the term "solvent" shall mean any material, most preferably a solution, which does not kill or render any microorganism present in a sample unviable for the purpose of flow cytometry fluorescent detection and which is filterable and renders the non-aqueous test sample filterable as well. In another embodiment, the solvent is be filterable and extracts any microorganisms which may be present in the sample such that they are trapped in a filter for presentation to a flow cytometry fluorescent detection system whether the original sample itself thereby becomes filterable or not. For sterility testing, the solvent should not render any present microorganisms unviable cytometry testing.

A rinsing fluid may comprise any rinsing fluid which results in the presence of naked organisms on the membrane suitable for cytometry analysis. It will be understood by one of skill in the art that the rinsing fluids identified in USP <71> are particularly suitable for the processes and methods of the present disclosure.

It has been determined that Isopropyl Myristate (IPM) is a suitable solvent for the purposes of the present disclosure for use in some embodiments. IPM is suitable for use in sterility testing of pharmaceutical preparations pursuant to USP <71>. Since IPM comports with USP <71>, no additional procedures or certifications are required. IPM will not kill bacteria or render microorganisms inviable which may be present in the drug compound being tested.

Referring now to FIG. 3, a schematic diagram of a cytometry preparation method for oil based (or unfilterable) samples according to aspects of the present disclosure is shown. Here a non-aqueous sample preparation 302 may be presented for sterility testing. The non-aqueous sample may be an ointment, cream, paste, or oil containing composition that has not been previously suitable for cytometry-based testing.

A quantity of isopropyl myristate (IPM) 304 is passed through a 0.45-micron filter 306 to ensure there are no particles that will be trapped by the test membrane at a later time. In some embodiments, the IPM 304 may be heated and/or maintained at 55° C. to increase mixability. The filtered and possibly warmed IPM 304 is then mixed at least 1:1 with the test sample 302. In some cases, a greater quantity of IPM may be used. The non-aqueous sample 302 combined with the IPM 304 may then be provided to the test membrane 106 and tested as previously described.

The sample 302 may be mixed with the IPM 304 in a number of ways. In some embodiments, the sample 302 and IPM 304 are mixed in a dual syringe arrangement. In other embodiments, the sample 302 is applied to the membrane 106 under vacuum concurrently with the IPM 304. Additional IPM (e.g., beyond the 1:1 ratio) may be applied to the membrane 106 as needed to ensure that the non-aqueous sample passes completely through the membrane 106, thus trapping all of the contaminant cells present in the sample 302.

It should be understood that the IPM 304 will not allow absolutely any oil or oil-based composition to pass through the membrane 106 within a timeframe that is suitable for testing, or without damaging the membrane due to excessive vacuum force that would be required to "pull" the composition through. Only some oils are suitable carriers for testing according to the present disclosure. By way of example, suitable oils are known to include grapeseed oil, mineral oil, ethyl oleate, medium chain triglycerides (triglycerides with fatty acids having aliphatic tails of 6-12 carbon atoms), and olive oil. Oils that are known at the present time to be unsuitable for methods according to the present disclosure are castor oil, peanut oil, cottonseed oil, almond oil, and corn oil.

It should be understood that even if a sample (e.g., a pharmaceutical or compounded product) is not based on one of the suitable oils per se, if it can be mixed with such a suitable oil as a carrier, it may be tested by the IPM preparation methods according to the present disclosure. In one embodiment, ointments for testing that are provided in a fatty base may be diluted by IPM 304 per the process above, possibly by heating to not more than 40° C. or, in another embodiment, not more than 44° C., down to 1% and then tested as described (e.g., by solid phase cytometry methods and systems). Such dilutions may not be stable for long periods of time but are known to be stable for a sufficient period of time to test via solid phase cytometry as described herein.

EXAMPLE 1

In the present example, step by step instructions are provided for one method of testing a non-aqueous sample (e.g., an oil-based sample) for biologically viable contaminants using a ScanRDI® machine and associated components combined with methodologies according to the present disclosure.

Scan RDI Filtration of Oil Based Samples 1.0 Protocol. The following protocol describes one method to perform the preparation, scanning and interpretation of the results 2.0 Apparatus 2.1 Filtration unit, 3 or 6 port manifolds. The unit should be capable of filtering 100 ml of sample through a 25 mm membrane on a sintered glass filter support and have a vacuum release valve. If Fluorassure Integrated Filtration Unit (FIFU) is selected, the manifolds need to be equipped with a FIFU filtration support kit (available from bioMerieux code: 415448).

2.2 A vacuum supply capable of sustaining −700 mbar with associated vacuum meter, vacuum reservoir, vacuum reservoir cap and 2 L vacuum flask.

2.3 Vortex mixer suitable for 1-40 mL tubes.

3.0 Reagents.

3.1 CSE, SCM, ChemSol A16, ChemSol B16, Fluid D, and ChemChrome V6 (light-sensitive and stored at 2-8° C.)

3.2 Isopropyl/Myristate (IPM)

3.3 Sterile water 4.0 Material 4.1 FIFU, sterile FIFU support pad: Ø 0.25 mm 4.2 0.22 µl syringe filter; sterile syringes: 3 mL, 12 mL, 20 mL, 35 mL, and 60 Ml 4.3 18½ gauge needles—with Luer Lock fittings 4.4 IL PES Filter Unit 0.2 µm 4.5 Adjustable pipettes: 20 µL-200 µL-1000 µL max delivery 4.6 Alcohol swabs 4.7 Decrimpers 4.8 Disposable pipette tips: 200 µL and 1000 µL 4.9 Forceps 4.10 Kimwipes 4.11 Sterile amber vials with screw top 4.12 Syringe caps 4.13 Sterile wipes 4.14 70% IPA wipes 5.0 Method 5.1. Obtain Solvent—Isopropyl Myristate (IPM)

5.2. Filter the appropriate amount using a vacuum filter with a 0.45 µm filter 5.2.1. If the filter used is not an appropriate receptacle for storing the filtered IPM, transfer to an appropriate container (i.e. amber vial).

5.2.1.1. IPM can be left in an incubator at 55° C. This w/ill enhance the effect IPM will have on oil-based formulations.

5.3. Mix the filtered IPM and the oil-based formulation in at least 1:1 dilution (some thicker oils such as cottonseed oil may need a higher ratio of IPM to oil) by one of the following two methods to obtain a mixture:

Mixing Method 5.3.1. Obtain two syringes, a Luer-lock connector, and a syringe tip.

5.3.1.1. Carefully remove the syringe plunger from the syringe barrel.

5.3.1.2. Place the plunger top face down onto the surface of the hood so the plunger seal is facing the air flow of the hood.

5.3.1.3. Attach the syringe tip to the syringe barrel. This will close the opening of the syringe barrel and allow you to pour sample into barrel.

5.3.1.4. Place appropriate amount of sample into the barrel of the syringe (based off of USP <71> Table 2 and Table 3) and then pour in the appropriate amount of filter IPM into the barrel of the syringe to achieve at least a 1:1 dilution.

5.3.1.5. Re-insert the plunger seal into the plunger barrel.

5.3.1.6. Carefully remove the syringe cap and attach the luer-lock connector.

5.3.1.7. Attach the other syringe to the connected leur-lock connector/syringe.

This will produce a closed system that will allow you to transfer the IPM/oil-based formulation between the two syringes, effectively mixing the two.

Once the sample and IPM has been mixed homogenously, place the sample in a FIFU unit for filtering.

Alternate Mixing Method 5.3.1. Place in IPM into FIFU unit then place in oil-based formulation. Make sure that this is in at least a 1:1 dilution. More IPM may be needed if it is not mixing appropriately.

5.3.1.1. The use of a sterile rod can be used to mix the IPM and oil-based formulation if necessary.

5.4. This filtering process may take up to 40 minutes depending on the formulation and oil used.

5.5. Rinse the membrane with a rinsing fluid (i.e. Fluid D) that is at least 20 mL more than the amount of sample filtered.

6.0 Preparing Sample for Flow Cytometry Fluorescent Detection System 6.1 Counterstaining and Pre-labelling of FIFU Membrane 6.1.1 Dispense 1 mL of CSE/CSM counterstain solution onto FIFU funnel. Leave the solution in contact with the membrane for 10 seconds.

6.1.2 Open the valve of the manifold and allow the CSE/CSM to filter through the FIFU membrane.

6.1.3 Leave the valve open and remove the funnel from FIFU carrier by moving the funnel from left to right and then pull it up. Close the valve and cap the FIFU membrane.

6.1.4 Pipette 420 µL of ChemSol A16 onto the pre-labeling pad.

6.1.5 Transfer and clip the FIFU membrane onto the labeling pad.

6.1.6 Transfer samples into incubator at the end of each run.

6.1.7 Incubate the samples at 30° C.±3° for 2-3.

6.1.8 Labelling of FIFU Membrane (after 2-3 hours of incubation)

6.1.8.1 Withdraw B16 from original vial and place into designated container, if applicable.

6.1.8.2 Pipette 200 µL of V6 using a 1:100 V6/B16 ratio and add 20 mL B16 vial.

6.1.8.3 Cap and mix the V6/B16, invert the vial 2-3 times.

6.1.8.4 Arrange the labeling pads in the hood, pipette 380 µl of V6/B16 labeling solution onto the labeling pads.

6.1.8.5 Remove the samples from the incubator. Clip off the labeling pad containing the ChemSol A16 and transfer FIFU membrane onto labeling pad saturated with V6/B16

6.1.8.6 Incubate the prepared samples at 30±3° C. for 45 minutes.

6.2 Transfer Samples to the Membrane Holder for Flow Cytometry Fluorescent Detection Analysis 7.0 Scan samples using ScanRDI® flow cytometry fluorescent detection system to obtain results.

7.1 Samples are scanned according to manufacturer protocol. Scan results are reported according to known protocol.

It is understood that a ScanRDI® machine, or any cytometry system, may need to be checked for proper functioning in order to operate successfully according to methods and systems of the present disclosure. Both positive and negative control procedures for commercially available cytometry systems are known to those of skill in the art and will not be repeated here. It should also be understood that incubation periods may not be needed in all embodiments and are not provided for cell division or culturing but to ensure that the viability marker has been adequately processed by viable biologics so as to produce adequate fluorescence under interrogation.

It is further to be understood that with respect to the systems and methods provided by the present disclosure for allowing non-aqueous samples to be successfully tested by cytometry system that in some embodiments, additional steps or componentry that do not alter the explicitly disclosed mechanisms and means of operation may be included. However, it should also be understood that, in some embodiments, the present disclosure should be taken as representing the entirety of the system and/or method. In other words, further processing of the sample beyond that disclosed in the present document should be taken as being excluded with respect to some embodiments. Whether or not additional steps or componentry are intended to be allowable with respect to any claim will be made clear by the language of the claim.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. A method for the detection of materials reactive to cytometry fluorescent detection in a viscous non-filterable, non-aqueous sample, the method comprising:
    obtaining the sample;
    obtaining a carrier oil;
    mixing the sample, carrier oil, and isopropyl myristate (IPM) to obtain a mixture;
    filtering the mixture through a membrane;
    presenting the membrane to a flow cytometry fluorescent detection system for analysis to obtain results; and
    detecting materials in the sample reactive to cytometry fluorescent detection based on the obtained results;
    wherein the carrier oil is selected from the group consisting of grapeseed oil, ethyl oleate, medium chain triglycerides, olive oil, and combinations thereof.

2. The method of claim 1 wherein the IPM is filtered before mixing with the sample.

3. The method of claim 1 wherein the materials reactive to flow cytometry fluorescent detection are viable microorganisms in a pharmaceutical preparation.

4. The method of claim 1 wherein a ratio of the IPM to the viscous non-filterable, non-aqueous sample in the mixture is at least 1:1.

5. The method of claim 4 wherein the IPM, the viscous non-filterable, non-aqueous sample, and the carrier oil are mixed in a closed system.

6. The method of claim 4 wherein the IPM, the viscous non-filterable, non-aqueous sample, and the carrier oil are mixed adjacent to the filter membrane.

7. The method of claim 6 wherein the IPM, the viscous non-filterable, non-aqueous sample, and the carrier oil are heated and stirred while mixing.

8. A method of preparing a non-aqueous, oil-based sample for cytometry detection of viable biological contaminants comprising:
    obtaining the oil-based, non-aqueous sample;
    combining the non-aqueous sample with isopropyl myristate (IPM) creating a mixture;
    and filtering the mixture through a cytometry test membrane to isolate contaminant cells onto the test membrane;
    wherein an oil of the oil-based sample is selected from the group consisting of grapeseed oil, ethyl oleate, medium chain triglycerides, olive oil, and combinations thereof.

9. The method of claim 8, further comprising providing a viability marker to the contaminant cells on the test membrane.

10. The method of claim 9, further comprising providing the viability marker as integrated with the test membrane.

11. The method of claim 8, further comprising filtering the IPM prior to combining with the oil-based, non-aqueous sample.

12. The method of claim 11, further comprising warming the filtered IPM prior to combining with the oil-based, non-aqueous sample.

13. The method of claim 8, wherein the step of combining the non-aqueous sample with the IPM creating a mixture is performed prior to placing the mixture onto the test membrane.

14. The method of claim 8, wherein the step of combining the non-aqueous sample with the IPM creating a mixture is performed in contact with the test membrane.

15. The method of claim 8, wherein the step of filtering the mixture through the cytometry test membrane to isolate contaminant cells onto the test membrane further comprises utilizing vacuum to filter the mixture through the cytometry test membrane.

16. The method of claim 8, further comprising counterstaining the cytometry test membrane after filtering the mixture therethrough.

17. The method of claim 8, further comprising performing cytometry testing by laser interrogation of the test membrane after filtering to determine a presence of viable biological contaminants.

* * * * *